(12) United States Patent
Bell et al.

(10) Patent No.: US 8,921,433 B2
(45) Date of Patent: Dec. 30, 2014

(54) PROCESS FOR THE CONVERSION OF SYNTHESIS GAS TO OXYGENATES CONTAINING C2+ ALCOHOLS

(75) Inventors: Peter Simpson Bell, Dunblane (GB); Leslie William Bolton, Fleet (GB); Benjamin Patrick Gracey, East Riding of Yorkshire (GB); Michael Keith Lee, East Riding of Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 1079 days.

(21) Appl. No.: 11/988,211

(22) PCT Filed: Jun. 29, 2006

(86) PCT No.: PCT/GB2006/002429
§ 371 (c)(1),
(2), (4) Date: Jan. 3, 2008

(87) PCT Pub. No.: WO2007/003909
PCT Pub. Date: Jan. 11, 2007

(65) Prior Publication Data
US 2009/0048354 A1 Feb. 19, 2009

(30) Foreign Application Priority Data

Jul. 6, 2005 (EP) .................................. 05254234
Dec. 19, 2005 (EP) .................................. 05257794

(51) Int. Cl.
*C07C 27/00* (2006.01)
*C07C 27/04* (2006.01)
*C07C 29/151* (2006.01)

(52) U.S. Cl.
CPC .................................. *C07C 29/1518* (2013.01)
USPC ........... 518/705; 518/702; 518/706; 518/707; 518/713; 568/885

(58) Field of Classification Search
USPC ........ 518/702, 705, 706, 707, 713; 568/902.2
See application file for complete search history.

(56) References Cited

U.S. PATENT DOCUMENTS

| | | | | |
|---|---|---|---|---|
| 4,111,837 A * | 9/1978 | Taylor | ........................... | 502/161 |
| 4,346,179 A * | 8/1982 | Sugier et al. | ................... | 518/707 |
| 4,424,384 A * | 1/1984 | Lin et al. | .................... | 568/902.2 |
| 4,472,526 A * | 9/1984 | Cornils et al. | ................ | 502/162 |
| 4,727,200 A * | 2/1988 | Wegman et al. | ............. | 568/902 |
| 4,894,394 A * | 1/1990 | Van Dijk et al. | ............. | 518/700 |
| 6,486,219 B1 * | 11/2002 | Janda et al. | ................... | 518/706 |
| 6,495,610 B1 * | 12/2002 | Brown | .......................... | 518/706 |
| 7,288,689 B2 * | 10/2007 | Janssen et al. | ................ | 585/640 |
| 2005/0107651 A1 * | 5/2005 | Sher et al. | ...................... | 585/639 |

OTHER PUBLICATIONS

International Search Report for PCT/GB2006/002429 mailed Oct. 11, 2006.
Iraqi Examination Report issued in corresponding Iraqi Patent Application No. 150/2006, dated May 29, 2009 (4 pgs), English Translation.
Lozano-Blanco, G., et al; "Fischer-Tropsch Synthesis: Development of a Microkinetic Model for Metal Catalysis"; *Oil & Gas Science and Technology*—*Rev. IFP*, vol. 61, No. 4, pp. 489-496 (2006).

(Continued)

*Primary Examiner* — Yate K Cutliff
(74) *Attorney, Agent, or Firm* — Nixon & Vanderhye P.C.

(57) ABSTRACT

Process for the conversion of carbon oxide(s) and hydrogen containing feedstocks into alcohols in the presence of a particulate catalyst.

25 Claims, 2 Drawing Sheets

(56) References Cited

OTHER PUBLICATIONS

Sinadinovic-Fiser, S.V, et al; "Simulation of the Fixed-Bed Reactor for Methanol Synthesis"; *Petroleum and Coal*, vol. 43, No. 1, pp. 31-34 (2001).

Dijk, H.A.J. van; "The Fischer-Tropsch synthesis: A mechanistic study using transient isotopic tracing"; by Henricus A.J. van Dijk. Eindhoven: Technische Universiteit Eindhoven, 2001. *Proefschrift*, (174pgs), ISBN 90-386-2732-7.

Xu, M., et al; "Carbon-Carbon Bond Formation Pathways in CO Hydrogenation to Higher Alcohols"; *Journal of Catalysis*, vol. 188, pp. 125-131 (1999).

Hindermann, J.P., et al; "Mechanistic Aspects of the Formation of Hydrocarbons and Alcohols from CO Hydrogenations"; *Catal. Rev. —Sci. Eng.*, vol. 35, No. 1, pp. 1-127 (1993).

Ph. Courty, et al; "Synthetic or Reformulated Fuels: a Challenge for Catalysis*"; *Oil & Gas Science and Technology—Rev. IFP*, vol. 54, No. 3, pp. 357-363 (1999).

Bianchi, C.L., et al; "Fischer-Tropsch synthesis on Co and Co(Ru-doped) ETS-10 titanium silicate catalysts"; *Catalysis Letters 41*, pp. 79-82 (1996).

\* cited by examiner

PROCESS FOR THE CONVERSION OF SYNTHESIS GAS TO OXYGENATES CONTAINING C2+ ALCOHOLS

This application is the U.S. national phase of International Application No. PCT/GB2006/002429 filed 29 Jun. 2006 which designated the U.S. and claims priority to European Patent Application Nos. 05254234.7 filed 6 Jul. 2005 and 05257794.7 filed 19 Dec. 2005, the entire contents of each of which are hereby incorporated by reference.

The present invention relates to an improved process for the conversion of carbon oxide(s) and hydrogen containing feedstocks into alcohols in the presence of a particulate catalyst.

In particular, the present invention relates to an improved process for the conversion of carbon oxide(s) (CO and $CO_2$) and hydrogen containing feedstocks, e.g. synthesis gas or syngas, into alcohols in the presence of a particulate modified molybdenum sulphide based catalyst, or a modified methanol based catalyst and/or a modified Fischer-Tropsch catalyst.

BACKGROUND OF THE INVENTION

U.S. Pat. No. 4,122,110 relates to a process for manufacturing alcohols, particularly linear saturated primary alcohols, by reacting carbon monoxide with hydrogen at a pressure between 20 and 250 bars and a temperature between 150 DEG and 400 DEG C., in the presence of a catalyst, characterized in that the catalyst contains at least 4 essential elements: (a) copper (b) cobalt (c) at least one element M selected from chromium, iron, vanadium and manganese, and (d) at least one alkali metal.

U.S. Pat. No. 4,831,060 relates to the production of mixed alcohols from carbon monoxide and hydrogen gases using a catalyst, with optionally a co-catalyst, wherein the catalyst metals are molybdenum, tungsten or rhenium, and the co-catalyst metals are cobalt, nickel or iron. The catalyst is promoted with a Fischer-Tropsch promoter like an alkali or alkaline earth series metal or a smaller amount of thorium and is further treated by sulfiding. The composition of the mixed alcohols fraction can be selected by selecting the extent of intimate contact among the catalytic components.

Journal of Catalysis 114, 90-99 (1988) discloses a mechanism of ethanol formation from synthesis gas over CuO/ZnO/Al2O3. The formation of ethanol from CO and H2 over a CuO/ZnO methanol catalyst is studied in a fixed-bed microreactor by measuring the isotopic distribution of the carbon in the product ethanol when 13C methanol was added to the feed.

SUMMARY OF THE INVENTION

It is an object of the present invention to provide an improved process in terms of selectivity and catalyst activity and operating life for the conversion of carbon oxide(s) and hydrogen containing feedstocks into alcohols in the presence of a particulate catalyst In particular, the present invention relates to an improved process in terms of selectivity and catalyst activity and operating life for the conversion of carbon oxide(s) and hydrogen containing feedstocks, e.g. synthesis gas or syngas, into alcohols in the presence of a particulate modified molybdenum sulphide based catalyst, or a modified methanol based catalyst and/or a modified Fischer-Tropsch catalyst.

DETAILED DESCRIPTION OF PREFERRED EMBODIMENTS

Figure 1:
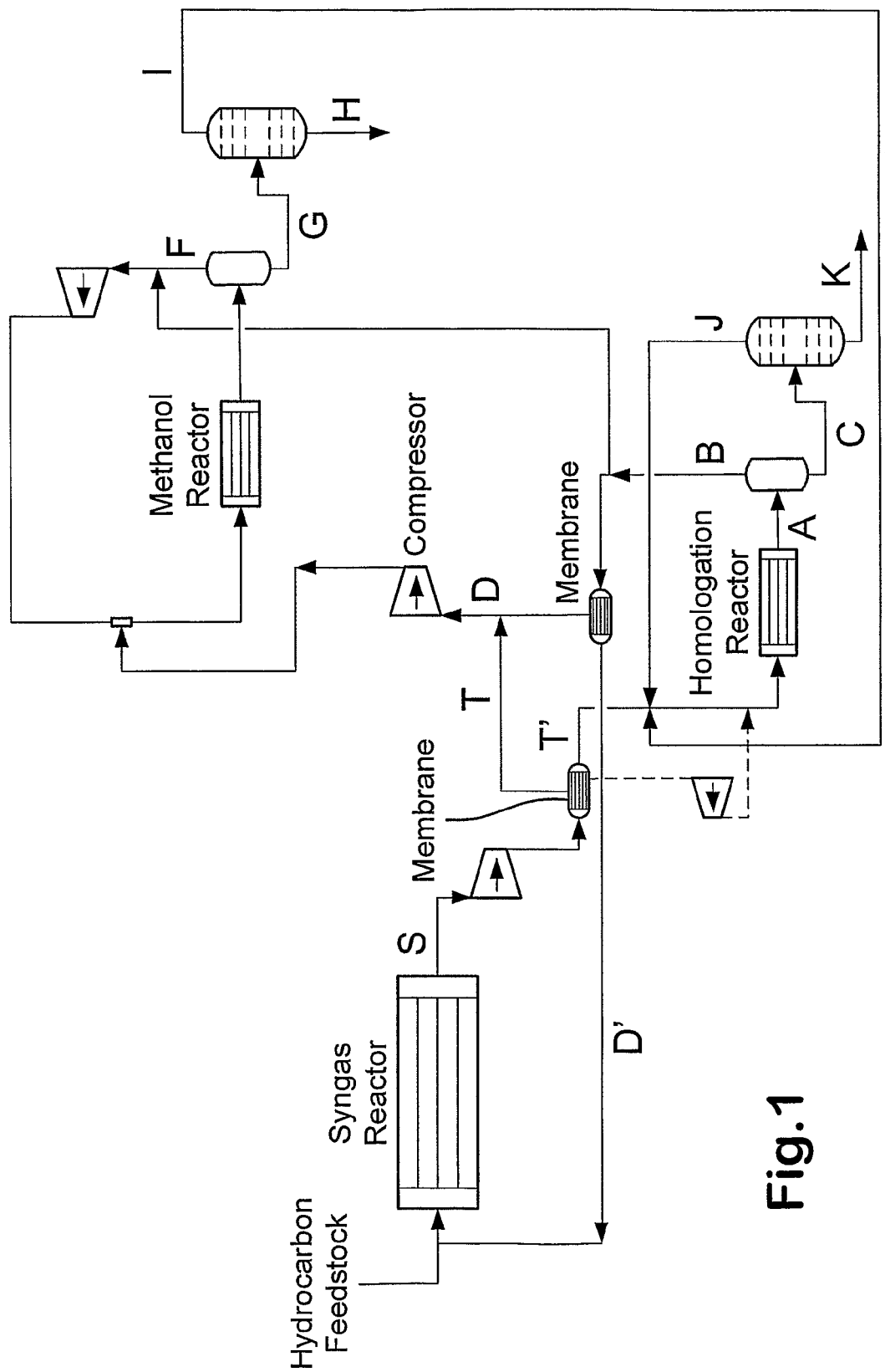
FIG. 1, represents one embodiment of a process scheme according to the present invention. This said embodiment comprises optional and/or preferred process steps according to the present invention. The letter references in FIG. 1 correspond to those used in the present description and appending claims.
Figure 2:
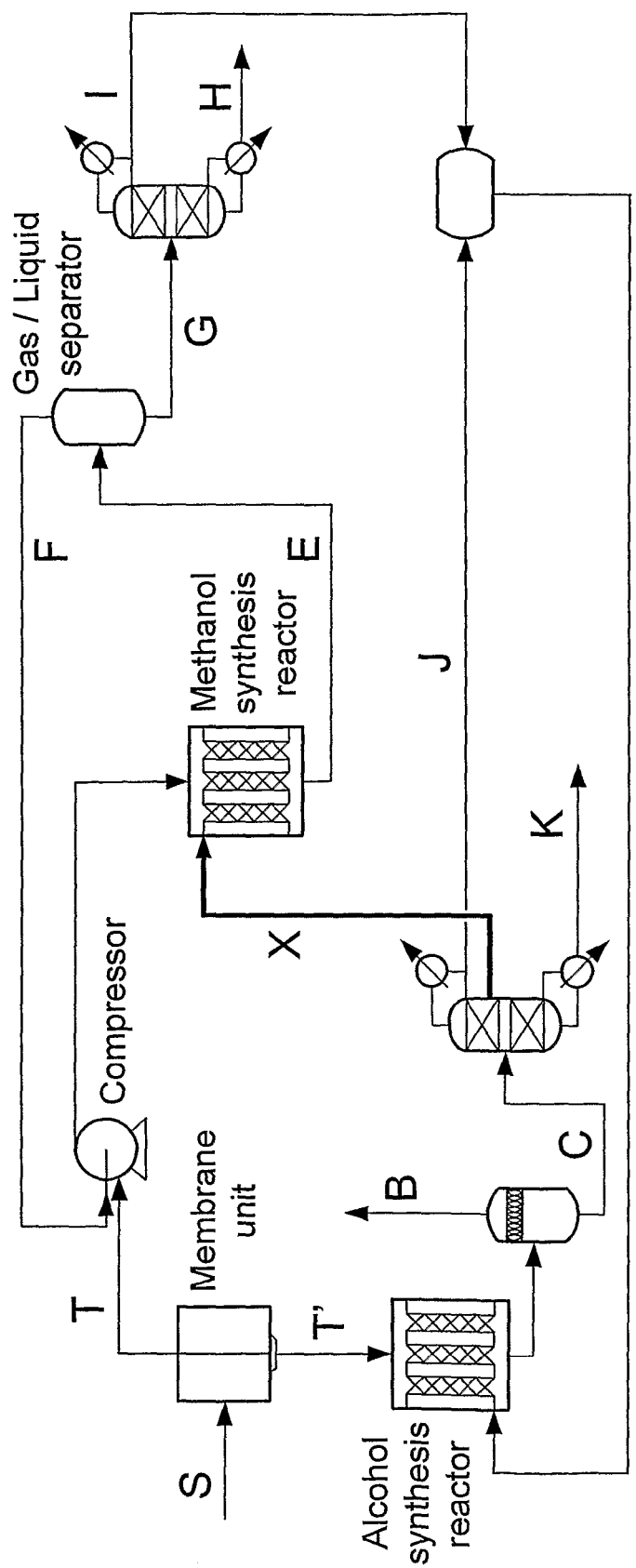
FIG. 2, represents another embodiment of a process scheme according to the present invention. This said embodiment comprises optional and/or preferred process steps according to the present invention. The letter references in FIG. 2 also correspond to those used in the present description and appending claims.

The present invention thus provides a process for the conversion, of carbon oxide(s) and hydrogen containing feedstocks, into alcohols in the presence of a particulate catalyst characterised by the following steps:

1. converting a carbon oxide(s) and hydrogen feed having a (H2-CO2):(CO+CO2) molar ratio comprised between 0.5 and 2.0, in the presence of a particulate catalyst in a homologation reactor under a temperature comprised between 150 and 400° C. and a pressure of 50 to 250 bar, into a stream A, comprising essentially alcohol(s), ester(s), H2, CO and CO2,
2. separating the alcohol stream A, into a stream B comprising H2, CO and CO2 and a stream C comprising the alcohol(s) and ester(s),
3. optionally separating the stream B into a H2 and CO2 depleted stream D' having a (H2-CO2):(CO+CO2) molar ratio of lower than 0.5 and a H2 and CO2 enriched stream D having a (H2-CO2):(CO+CO2) molar ratio higher than 3,
4. converting a CO/CO2/H2 feed (optionally comprising stream D) having a (H2-CO2):(CO+CO2) molar ratio higher than 3 in a methanol reactor into a stream E comprising essentially methanol, water, H2, CO and CO2,
5. separating stream E into stream F comprising H2, CO and CO2 and stream G comprising methanol and water,
6. separating stream G into stream H consisting essentially of water and stream I comprising essentially methanol,
7. reintroducing stream I into the homologation reactor of step 1, and
8. recovering a stream C comprising an increased weight content of total ethanol and propanol(s).

According to a preferred embodiment of the present invention (step 9), the recovered stream C is separated into a stream J comprising essentially methanol which is then preferably recycled into the homologation reactor of step 1, and a stream K comprising essentially the ethanol and propanol(s) alcohols.

According to another preferred embodiment of the present invention (step 10), the recovered stream C is separated into a stream J comprising essentially methanol which is then preferably recycled into the homologation reactor of step 1, a stream K comprising essentially the ethanol and propanol(s) alcohols, and a stream X comprising essentially the ester(s) which are then preferably recycled into the methanol reactor of step 4. The applicants have unexpectedly found that by using this preferred embodiment of ester(s) recycling into the methanol reactor in the integrated flow sheet process of the present invention, it was possible to control the ratio of propanol to ethanol produced in stream A. Thus, the present invention also relates to a process for controlling the ratio of propanol to ethanol produced in the claimed integrated process for producing alcohols when using hereabove defined step 10. This discovery is particularly advantageous, since now; the said process is highly economically advantageous compared to existing technologies in the field for producing n-propanol, which incur large operating expenses.

According to a preferred embodiment, the present invention provides a process for the conversion of hydrocarbons to alcohols comprising the steps of:
   a. converting hydrocarbon in a syngas reactor into a stream S consisting of a mixture of carbon oxide(s) and hydrogen having a (H2-CO2):(CO+CO2) molar ratio of at least 2,
   b. separating stream S into a stream T' having a (H2-CO2):(CO+CO2) molar ratio between 0.5 and 2.0 and a stream T having a (H2-CO2):(CO+CO2) molar ratio higher than 3,
   c. using stream T' as the carbon oxide(s) and hydrogen feed source of step 1 of claim 1, and converting it in the homologation reactor into stream A,
   d. using stream T as the carbon oxide(s) and hydrogen feed of step 4 of claim 1 (optionally also comprising stream D of step 3 of claim 1), and converting the (mixed) stream T (and D) in the methanol reactor into stream E, and
   e. proceeding with the steps of any of claims 1 to 3.

According to a preferred embodiment of the present invention, the alcohols produced are mainly methanol, propanol, ethanol and butanols (predominately n-butanol and isobutanol); said methanol, propanols (predominately n-propanol with low amounts of iso-propanol) ethanol and butanol preferably represent together at least 50% by weight of the liquid products obtained from the homologation reactor (stream A), more preferably at least 75% by weight, most preferably at least 90% by weight.

According to another embodiment of the present invention, the ester(s) and the optional water which are also produced in the homologation reactor preferably represent together with the alcohol(s) at least 80% by weight of the liquid products obtained from the homologation reactor (stream A), preferably at least 90 wt %, more preferably at least 95 wt %, most preferably at least 99 wt %.

According to another embodiment of the present invention, the ester(s) produced and optionally recycled are mainly methyl acetate, ethyl acetate, methyl formate, or ethyl formate, or mixture(s) thereof.

The target alcohols produced according to the present invention preferably consist of ethanol or propanol(s) or, more preferably, a mixture thereof, wherein the molar ratio of ethanol to propanol(s) is preferably comprised between 2 and 5. Said total target alcohol(s) represent preferably at least 40% by weight of the alcohols present in stream A, more preferably at least 50% by weight, most preferably at least 60% by weight.

The particulate catalyst according to the present invention for the conversion of carbon oxide(s) and hydrogen containing feedstocks, e.g. synthesis gas or syngas, to alcohols is preferably a particulate modified molybdenum sulphide based catalyst, or a rhodium catalyst, or a modified methanol based catalyst and/or a modified Fischer-Tropsch catalyst.

The process according to the present invention has proven to be highly beneficial to the alcohols selectivity, especially the ethanol selectivity, while simultaneously increasing catalyst activity and improving operating life.

Beyond these unexpected advantages, other advantages have also been found when applying the present process invention, amongst others:

(i) less waste, less by-products and thus higher carbon efficiency.
   (ii) less capital, fewer separations, reduced storage tanks.
   (iii) no corrosion and metallurgy constraints due to the potential hydrolysis of the esters during subsequent purification and storage stages As indicated, the particulate catalyst used in the homologation reactor is preferably a modified molybdenum sulphide based catalyst, and/or a modified methanol based catalyst and/or a precious metal based catalyst such as a rhodium catalyst, and/or a modified Fischer-Tropsch catalyst.

Preferably, the catalyst used in the homologation reactor contains at least molybdenum and/or cobalt; it is preferably promoted by the addition of an alkali metal salt.

Mixed molybdenum sulphide based catalysts are preferred; a salt of a group I or II alkali metal or alkaline earth metal more preferred are group I alkali metals such as cesium and potassium, especially potassium carbonate, potassium nitrate, potassium acetated and hydroxide are the preferred promoters.

Most preferably, the catalyst used is a molybdenum sulphide based catalysts containing cobalt, the molybdenum to cobalt molar ratio being preferably comprised between 1.5 and 2.5, more preferably 2; the said molybdenum sulphide based catalysts containing cobalt is most preferably promoted with potassium ions (K2CO3 may be used in the preparation but not in the catalyst in this form). The preferred potassium of use has a Mo molar ratio of less than 0.5 but greater than 1.75; preferably more than 0.9 and less than 1.3.

According to a preferred embodiment, after using the said catalyst of the present invention, the resulting product (essentially stream A) is subsequently treated, so as to remove any sulphur present in the stream as a result of using the said catalyst. This may be performed by, for example, the use of sulphur guard beds.

Any hydrocarbon-containing feed stream that can be converted into a feedstock comprising carbon monoxide and hydrogen, most preferably a synthesis gas (or "syngas"), is useful in the processes of the invention.

The hydrocarbon feedstock used for syngas generation is preferably a carbonaceous material, for example biomass, plastic, naphtha, refinery bottoms, smelter off gas, municipal waste, coal, coke and/or natural gas, coal and natural gas being the preferred ones, most preferably natural gas.

Processes for producing mixtures of carbon oxide(s) and hydrogen (synthesis gas) are well known. Each has its advantages and disadvantages and the choice of using a particular reforming process is dictated by economic and available feed stream considerations, as well as by the desired mole ratio of H2:CO in the feedstock resulting from the reforming reaction. The synthesis gas may be prepared using any of the processes known in the art including partial oxidation of hydrocarbons (POX), steam reforming (SR), advanced gas heated reforming (AGHR), microchannel reforming (as described in, for example, U.S. Pat. No. 6,284,217 which is herein incorporated by reference), plasma reforming, autothermal reforming (ATR) and any combination thereof. A discussion of these synthesis gas production technologies is provided in "Hydrocarbon Processing" V 78, N. 4, 87-90, 92-93 (April 1999) and "Petrole et Techniques", N. 415, 86-93 (July-August 1998). It is also envisaged that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187-196. Alternatively, the synthesis gas may be obtained by short contact time catalytic partial oxidation of hydrocarbonaceous feedstocks as described in EP 0303438. Preferably, the synthesis gas is obtained via a "Compact Reformer" process as described in "Hydrocarbon Engineering", 2000, 5, (5), 67-69; "Hydrocarbon Processing", 79/9, 34 (September 2000); "Today's Refinery", 15/8, 9 (August 2000); WO 99/02254; and WO 200023689.

The syngas used in the present invention is preferably obtained via a methane steam reforming (MSR) or via the combination of methane steam reforming with a partial oxidation of hydrocarbons.

Typically, for commercial syngas production the pressure at which the synthesis gas is produced ranges from approximately 2 to 100 bar, preferably 20 to 75 bar, and the temperature at which the synthesis gas exits the reformer ranges from approximately 700° C. to 1100° C. The synthesis gas contains a molar ratio of hydrogen to carbon oxide, which is dependent on the syngas feedstock, ranging from 0.8 to 3.

According to the present invention, the (H2-CO2):(CO+CO2) molar ratio of stream S obtained from the syngas reactor is of at least 2, preferably between 2.1 and 3.0 and most preferably between 2.4 and 2.8.

According to the present invention, the (H2-CO2):(CO+CO2) molar ratio of the feed (preferably T') introduced into the homologation reactor is comprised between 0.5 and 2.0, preferably comprised between 0.8 and 1.3.

According to an embodiment of the present invention, the (H2-CO2):(CO+CO2) molar ratio of the feed introduced into the homologation reactor is comprised between 0.9 and 1.1.

The alcohol synthesis catalysts, can also catalyse the water gas shift reaction. A consequence of this is that hydrogen and carbon dioxide are interconvertable with carbon monoxide and water. For high partial pressures of carbon dioxide (at or above the water gas shift equilibrium), carbon dioxide can act as a carbon monoxide source and a hydrogen sink and this can effect the apparent preferred syngas ratio. Useful feed streams include natural gas (mainly methane, but natural gas composition can vary depending on location and source), naphtha, refinery off-gas, LPG, gas oil, vacuum residuals, shale oils, asphalts, various types of fuel oils, coal based/lignin deposits and hydrocarbon containing process recycle streams. According to a preferred embodiment of the present invention, methane is used as the hydrocarbon-containing feed stream to be converted into carbon oxides(s) and H2.

Feedstocks comprising carbon monoxide and hydrogen, e.g. synthesis gas, may undergo purification prior to being fed to any reaction zones. Synthesis gas purification may be carried out by processes known in the art. See, for example, Weissermel, K. and Arpe H.-J., Industrial Organic Chemistry, Second, Revised and Extended Edition, 1993, pp. 19-21.

The particular reaction conditions for the homologation reactor embodiments described below are not narrowly critical and can be any effective reaction conditions sufficient to produce the target alcohols. The exact reaction conditions will be governed by the best compromise between achieving high catalyst selectivity, activity, lifetime and ease of operability, as well as the intrinsic reactivity of the starting materials in question and the stability of the starting materials and the desired reaction product to the reaction conditions.

In one embodiment of this invention, feedstock comprising the desired molar ratio of (H2-CO2):(CO+CO2) is fed into the homologation reactor at a controlled rate and the reaction is carried out in a reaction zone under controlled conditions of temperature and pressure in the presence of a catalyst to convert the feedstock into the target alcohols.

The temperature in the homologation reaction zone is selected from the range of starting from about 150° C. to about 400° C. (e.g. 200° C. to 400° C. The gas hourly space velocity (GHSV) of the feedstock (liters of feedstock/hr/liter of catalyst at STP) passing through the reaction zone can vary significantly, depending upon a variety of factors such as, for example, reaction conditions, composition of the feedstock and quantity and type of catalyst being used. Preferably, the GHSV can be maintained at any rate in the range of from about 1 to about 30,000 hr-1 or more, preferably will be maintained at a rate of at least about 500 hr-1, and more preferably will be maintained at a rate of at least 1,000 hr-1. The pressure in the homologation reaction zone may be selected from the range of from about 50 to 250 bar (e.g. 50 to 200 bar), preferably a pressure in the range of from about 80 to 150 bar.

The hydrogen and carbon monoxide partial pressures should be sufficient to enable the production of the target alcohols. Hydrogen and carbon monoxide may be fed separately to the conversion reactor or, preferably in combination, e.g., as synthesis gas. For purposes of this invention, GHSV is gas hourly space velocity which is the rate of gas flow over the catalyst. It is determined by dividing the volume of gas (at 25° C. and 1 atmosphere) which passes over the catalyst in one hour by the volume of the catalyst. LHSV is liquid hourly space velocity which is the rate that the liquid organic substrate is fed to the conversion reactor. It is determined by dividing the liquid volume pumped in one hour by the volume of catalyst.

The homologation reaction (conversion to alcohols) can be carried out by passing the mixture of hydrogen and carbon monoxide over the conversion catalyst as a vapour phase reaction or as a liquid phase reaction, e.g., slurry reaction or trickle bed fluidized bed reactor, single or staged adiabatic reactors, multi-tubular, torodial.

The reaction may be carried out in any appropriate reactor, e.g. a tubular reactor using a fixed bed of the catalyst. The reactants may be fed to the catalyst by feeding down or up, or a combination of both, to a fixed bed located in a tubular reactor. The reaction may be effected in a dynamic bed of the catalyst. In such a reaction, the bed of catalyst is moving such as in the case of a fluid bed of the catalyst. The alcohols conversion reactor may preferably be chosen amongst tubular, multitubular, slurry, moving bed, fluidised bed, radial bed, multibed or reactive distillation reactor. It is preferably a multibed or multitubular vapour phase reactor.

According to the present invention, the process operated in the methanol reactor, comprises converting a carbon oxide(s) and hydrogen feed (optionally comprising stream T) having a (H2-CO2):(CO+CO2) molar ratio higher than 3 in a methanol reactor, into a methanol and water stream E.

The following description relates to one possible embodiment of the conversion to methanol process step; contacting synthesis gas with a catalyst at a temperature in the range from 80 to 300° C. and a pressure of from 25 to 125 bars.

In one pass the conversion of the carbon oxide(s) within the synthesis gas is limited due to the thermodynamic equilibrium being reached; therefore, after methanol and water are condensed out and removed, the remaining synthesis gas can advantageously be recycled to the reactor. The make-up synthesis gas is brought to the desired pressure (25-125 MPa) in a multistage compressor. The unreacted recycle is added before the recycle stage. A heat exchanger transfers energy from the hot gas leaving the reactor to the gas entering the reactor. The exothermic formation of methanol takes place in the reactor at 200-300° C. The heat of reaction can be dissipated in one or more stages. The mixture is cooled further after passing through the heat exchanger; the heat of condensation of methanol and water can be utilized at another point in the process.

The methanol reactor may be either adiabatic (e.g., ICI) or quasi-isothermal (e.g., Lurgi), examples of such reactors and methanol processes can be found in 'Methanol', Ullmann's Encyclopedia of Industrial Chemistry, Jun. 15, 2000, which is hereby incorporated by reference.

The operation of the exothermic methanol production process at temperatures above 300° C. tends to produce increasing amounts of alkanes, thereby decreasing the selectivity to methanol. It is therefore preferred to operate at a temperature in the range from 180 to 270° C. for the highest selectivities to methanol. Preferably the operating pressure is in the range from 20 to 100 bars. The Gas Hourly Space Velocity (GHSV) may be varied over a wide range, for example in the range from 1000 to 350,000 hour~I.

According to a preferred embodiment of the present invention, the alcohols (essentially methanol and some higher alcohols, e.g ethanol) produced in the methanol reactor represent together with the water at least 90 wt %, more preferably at least 95 wt %, most preferably at least 99 wt % of stream G.

According to step 2 of the present invention, the stream A is separated into a stream B comprising $H_2$, CO and $CO_2$ and a stream C comprising the alcohols and ester(s). The stream B can be flared, used as fuel, fed to syngas generation or fed to the methanol synthesis reactor, or used as a combination of the above.

According to an embodiment of the present invention, the stream B is separated into a $H_2$ and $CO_2$ depleted stream D' having a ($H_2$-$CO_2$):(CO+$CO_2$) molar ratio lower than 0.5 and a $H_2$ and $CO_2$ enriched stream D having a ($H_2$-$CO_2$):(CO+$CO_2$) molar ratio higher than 3. Said stream D is then preferably used as a feed to the methanol synthesis reactor. Said feed D' is then either flared, or used as fuel, or fed to syngas generation, or used as a combination of the above.

According to a preferred embodiment of the present invention, the optional separation of stream B into streams D and D' and the separation of step b according to the present invention are respectively performed by using a $H_2$/$CO_2$ membrane.

The $H_2$/$CO_2$ membranes that can be used according to the present invention are preferably membranes based on a polymer packaged as a hollow fiber. A differential pressure is established across the said membrane. All gases permeate from the high-pressure (feed) side of the membrane to the low-pressure (permeate) side, and the difference in the permeation rates of gases provides the separation. Molecules that permeate quickly, such as $H_2$, He, and $H_2S$, can be separated from molecules that permeate more slowly, such as CO, $CH_4$ and $N_2$. Such membrane technologies can be found in 'Purification and Recovery Options for Gasification' D. J. Kubek, E. Polla, F. P. Wilcher, UOP, 1996, and is hereby incorporated by reference.

Optionally, after the gas is passed through the membrane some remixing of the permeate with the retained material may be employed in order to adjust the syngas ratio.

The optional separation of stream B into streams D and D', is performed in order to obtain
a hydrogen and $CO_2$ rich syngas stream D which is then preferably used as a feed (optionally together with stream T) to the methanol reactor, and
a CO rich syngas stream D' which is then preferably recycled to the syngas conversion reactor as feedstock and/or fuel.

According to another embodiment of the present invention, at least part of this stream D' is also recycled to the homologation reactor.

The separation under step b is performed in order to obtain
a hydrogen rich syngas stream T used as a feed (optionally together with all or part of stream D) to the methanol reactor, and
a hydrogen lean syngas stream T' used as a feed to the homologation reactor.

Stream T has a ($H_2$-$CO_2$):(CO+$CO_2$) molar ratio higher than 3, and preferably contains more than 90% moles of $H_2$.

Stream T' has a ($H_2$-$CO_2$):(CO+$CO_2$) molar ratio comprised between 0.5 and 2.0.

According to a preferred embodiment of the present invention, the separation of step 2 and the separation of step 5 are performed by using a common means of gas liquid separation such as a knockout drum or a cyclone.

According to another embodiment of the present invention the separation under step 2 is performed in order to obtain
a $H_2$, CO and $CO_2$ stream B which is then preferably separated according to optional step 3, and
an alcohol(s) and ester(s) stream C.

According to a further embodiment of the present invention, at least part of stream B is also used as a feed to the methanol reactor.

The separation under step 5 is performed in order to obtain
a $H_2$, CO and $CO_2$ stream F, and
a methanol and water stream G.

According to a preferred embodiment of the present invention, the applicants have unexpectedly found that by recycling stream F (which comprises the unreacted syngas from the methanol reactor) in the methanol reactor, it was possible to increase the efficiency of the methanol produced in the methanol reactor.

According to a preferred embodiment of the present invention, the separation of steps 6 and/or 9 and/or 10 are performed respectively by using distillation columns.

The separation under step 6 is performed in order to separate water (stream H) from the methanol stream G so as to obtain a methanol stream I which is recycled back into the homologation reactor.

According to another embodiment of the present invention, at least part of this stream I can be sold on the methanol market.

The optional separation under step 9, is performed in order to separate methanol (stream J) from the alcohols stream C so as to obtain the target alcohols (stream K) that then can then be recovered. According to another embodiment of the present invention, at least part of stream J—preferably all of stream J—is recycled back into the homologation reactor.

The optional separation of step 10, is performed in order to separate stream C into a stream J, consisting essentially of methanol; a stream X, comprising ester(s) and a stream K comprising essentially ethanol and propanol(s). Again, preferably at least part of stream J—most preferably all of stream J—is recycled back into the homologation reactor.

According to a preferred embodiment of the present invention, the Applicants have unexpectedly found that by performing the optional recycling of stream X, according to step 10, in the integrated process as claimed in the present invention, it was possible to increase the ratio of propanol to ethanol produced in the recovered stream K, and therefore presented a clear advantage over other alcohol production methods. While not wishing to be bound by this theory, the Applicants believe that the ester(s) recycled in the methanol reactor are converted into alcohols (e.g. ethanol) in the said methanol reactor and then recycled back together with the methanol into the homologation reactor, thereby producing an increased ratio of propanol(s) versus ethanol after homologation. This is very surprising because the methanol still preferably represents more than 80 wt %, more preferably more than 90 wt %, most preferably more than 95 wt %, of the total alcohols present in stream G according to this embodiment.

The invention claimed is:

1. Process for the conversion of carbon oxide(s) and hydrogen containing feedstocks into alcohols in the presence of a particulate catalyst comprising the following steps:
   (a) converting a carbon oxide(s) and hydrogen feed having a (H2-CO2):(CO+CO2) molar ratio comprised between 0.5 and 2.0, in the presence of a particulate catalyst in a homologation reactor under a temperature comprised between 150 and 400° C. and a pressure of 50 to 250 bar, into a stream A, comprising essentially alcohol(s), ester(s), H2, CO and CO2,
   (b) separating the alcohol stream A, into a stream B comprising H2, CO and CO2 and a stream C comprising the alcohol(s) and ester(s),
   (c) optionally separating the stream B into a H2 and CO2 depleted stream D' having a (H2-CO2):(CO+CO2) molar ratio of lower than 0.5 and a H2 and CO2 enriched stream D having a (H2-CO2):(CO+CO2) molar ratio higher than 3,
   (d) converting a CO/CO2/H2 feed (optionally comprising stream D) having a (H2-CO2):(CO+CO2) molar ratio higher than 3 in a methanol reactor into a stream E comprising essentially methanol, water, H2, CO and CO2,
   (e) separating stream E into stream F comprising H2, CO and CO2 and stream G comprising methanol and water,
   (f) separating stream G into stream H consisting essentially of water and stream I comprising essentially methanol,
   (g) reintroducing stream I into the homologation reactor of step (a), and
   (h) recovering a stream C comprising an increased weight content of total ethanol and propanol(s).

2. Process (step (i)) according to claim 1 wherein the stream C from step (h) is separated into
   a stream J comprising essentially methanol which is then recycled into the homologation reactor of step (a), and
   a stream K comprising essentially the ethanol and propanol(s) alcohols.

3. Process (step (j)) according to claim 1 wherein the recovered stream C from step (h) is separated into
   a stream J comprising essentially methanol,
   a stream K comprising essentially the ethanol and propanol(s) alcohols, and
   a stream X comprising essentially the ester(s).

4. Process for the conversion of hydrocarbons to alcohols comprising the process of claim 1, wherein the process additionally comprises the steps of:
   a. converting hydrocarbon in a syngas reactor into a stream S consisting of a mixture of carbon oxide(s) and hydrogen having a (H2-CO2):(CO+CO2) molar ratio of at least 2,
   b. separating stream S into a stream T' having a (H2-CO2):(CO+CO2) molar ratio between 0.5 and 2.0 and a stream T having a (H2-CO2):(CO+CO2) molar ratio higher than 3,
   c. using stream T' as the carbon oxide(s) and hydrogen feed source of step (a) of claim 1, and converting it in the homologation reactor into stream A, and
   d. using stream T as the carbon oxide(s) and hydrogen feed of step (d) of claim 1, and converting the (mixed) stream T (and D) in the methanol reactor into stream E.

5. A process for the conversion of hydrocarbon to alcohols according to claim 1 whereby stream F is recycled back into the methanol reactor of step (d).

6. A process for the conversion of hydrocarbon to alcohols according to claim 4 whereby the (H2-CO2):(CO+CO2) molar ratio of stream S obtained from the syngas reactor is of at least 2.

7. A process for the conversion of hydrocarbons to alcohols according to claim 4 whereby stream T has a (H2-CO2):(CO+CO2) molar ratio of higher than 3, and contains more than 90% moles of H2.

8. A process for the conversion of hydrocarbons to alcohols according to claim 1 whereby the particulate catalyst used in the homologation reactor is selected from the group consisting of a molybdenum sulphide based catalyst, a methanol based catalyst and a Fischer-Tropsch catalyst.

9. A process for the conversion of hydrocarbons to alcohols according to claim 1 whereby the catalyst used in the homologation reactor contains at least molybdenum and/or cobalt and/or copper.

10. A process for the conversion of hydrocarbons to alcohols according to claim 1 whereby the resulting product stream from the homologation reactor of step (a) (stream A) is treated so as to remove any sulphur present.

11. A process for the conversion of hydrocarbons to alcohols according to claim 10, whereby said removal of the sulphur is performed by the use of a sulphur guard bed.

12. A process for the conversion of hydrocarbon to alcohols according to claim 1 whereby the (H2-CO2):(CO+CO2) molar ratio of the feed introduced into the homologation reactor is comprised between 0.5 and 2.0.

13. A process for the conversion of hydrocarbons to alcohols according to claim 4 whereby the optional separation of step (c) and the separation of step b wherein stream S is separated into a stream T' having a (H2-CO2):(CO+CO2) molar ratio between 0.5 and 2.0 and a stream T having a (H2-CO2):(CO+CO2) molar ratio higher than 3 are respectively performed by using a H2/CO2 membrane.

14. A process for the conversion of hydrocarbons to alcohols according to claim 13 whereby the H2/CO2 membrane is based on a polymer packaged as a hollow fiber.

15. A process for the conversion of hydrocarbons to alcohols according to claim 1 whereby the optional separation under step (c) is performed.

16. A process for the conversion of hydrocarbons to alcohols according to claim 4 whereby stream D' is recycled to the syngas conversion reactor as feedstock and/or fuel and optionally at least part of it is recycled to the homologation reactor.

17. A process for the conversion of hydrocarbons to alcohols according to claim 1 whereby at least part of stream B is also used as a feed to the methanol reactor.

18. A process for the conversion of hydrocarbons to alcohols according to claim 1 whereby at least part of stream J is recycled back into the homologation reactor.

19. Process according to claim 3 wherein stream J comprising essentially methanol is recycled into the homologation reactor of step and stream X comprising essentially the ester(s) is recycled into the methanol reactor of step (d).

20. Process according to claim 4 wherein in step d, stream T used as the carbon oxide(s) and hydrogen feed of step (d) of claim 1 also comprises stream D of step (c) of claim 1.

21. A process for the conversion of hydrocarbon to alcohols according to claim 6 whereby the (H2-CO2):(CO+CO2) molar ratio of stream S obtained from the syngas reactor is between 2.1 and 3.0.

22. A process for the conversion of hydrocarbon to alcohols according to claim 21 whereby the (H2-CO2):(CO+CO2) molar ratio of stream S obtained from the syngas reactor is between 2.4 and 2.8.

23. A process for the conversion of hydrocarbons to alcohols according to claim 9 whereby the catalyst is promoted by the addition of an alkali metal salt.

24. A process for the conversion of hydrocarbon to alcohols according to claim 12 whereby the (H2-CO2):(CO+CO2) molar ratio of the feed introduced into the homologation reactor is comprised between 0.8 and 1.3.

25. A process for the conversion of hydrocarbons to alcohols according to claim 18 whereby all of stream J is recycled back into the homologation reactor.

* * * * *